United States Patent [19]
Smith et al.

[11] Patent Number: 4,558,145
[45] Date of Patent: Dec. 10, 1985

[54] PREPARATION OF FE CHELATES

[75] Inventors: Nelson Smith, Mobile; Joseph W. Stutts, Jackson, both of Ala.

[73] Assignee: Ciba Geigy Corporation, Ardsley, N.Y.

[21] Appl. No.: 544,296

[22] Filed: Oct. 21, 1983

[51] Int. Cl.$^4$ .............................................. C07F 15/02
[52] U.S. Cl. .................................................. 556/148
[58] Field of Search .......................... 260/439 R, 429 J

[56] References Cited

U.S. PATENT DOCUMENTS

| | | | |
|---|---|---|---|
| 2,859,104 | 11/1958 | Kroll | 260/429 J |
| 3,051,563 | 8/1962 | Bersworth | 260/429 J |
| 3,080,410 | 3/1963 | Le Blanc | 260/439 R |
| 3,115,511 | 12/1963 | Singer et al. | 260/429 J |
| 3,758,534 | 9/1973 | Popper et al. | 260/429 J |
| 3,758,540 | 9/1973 | Martell | 260/439 R |
| 3,767,689 | 10/1973 | Donovan et al. | 260/439 R |
| 4,076,621 | 2/1978 | Hardison | 423/573 R |

OTHER PUBLICATIONS

Chemical Abstracts 86 95323v (1977).
Chemical Abstracts 82 174043z (1975).
Chemical Abstracts 68 4520w (1968).
Chemical Abstracts 86 194429r (1977).
Chemical Abstracts 89 117257t (1978).

*Primary Examiner*—Helen M. S. Sneed
*Attorney, Agent, or Firm*—Karl F. Jorda

[57] ABSTRACT

A new process for the preparation of HO-EDTA.FE (5% Fe) is disclosed. It is based on the oxidation of Fe° by nitric acid in the presence of HO-EDTA Na$_3$ to generate the chelate in the Fe$^{+2}$ state. The Fe$^{+2}$ chelate is then converted to the desired Fe$^{+3}$ chelate by air oxidation.

8 Claims, No Drawings

PREPARATION OF FE CHELATES

FIELD OF THE INVENTION

This invention relates to a process for preparing a ferric chelate and more specifically for preparing a ferric chelate of the formula

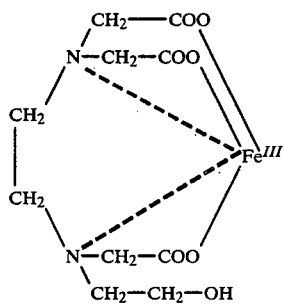

BACKGROUND OF THE INVENTION

Metal chelates are useful sources for the correction of minor elemental deficiencies in soils used for growing ornamentals, fruits and vegetables. Iron is an essential micro-nutrient. While it is widely distributed in soils and fertilizers, it seldom needs to be applied to crops except in alkaline soils. Many species of plants become chlorotic in such soils unless fertilized with salts soluble under alkaline conditions. An example, is the requirement for such a soluble iron source by pineapples grown on manganiferous soils.

Certain organic chemicals, known as chelating agents, form ring compounds in which a polyvalent metal such as iron is held firmly between two or more bridge atoms. Such bonding, by ring formation, is known as chelation. Among the best chelating agents known are N-(2-hydroxyethyl)ethylenediaminetriacetic (HO-EDTA) acids. They successfully chelate iron, copper, zinc, manganese and calcium. Iron, copper and zinc are agriculturally important but are converted to insoluble hydroxides or insoluble basis salts at levels above about pH 6 or 7 HO-EDTA chelates keep these trace elements soluble and available to the plants in soils up to and over about pH 10 in the case of iron.

Commercially, the preferred iron chelate source has been ferric HO-EDTA.

It is available as a 5% $Fe^{+3}$ (equivalent) aqueous solution, or as the crystallized salt. It is also known as HO-EDT.Iron III; or [(N-(2-hydroxyethyl)-ethylenedinitrilo)triaceto] ferrate (CAS Registry No. 17084-02-5). Its formula is accepted as

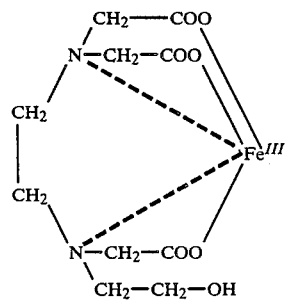

This compound has been commercially prepared by combining a trisodium hydroxy-EDTA (Merck Index 9622 - CAS Registry No. 139-89-9) with $Fe_2(SO_4)_3$. This HO-EDTA salt has the accepted formula

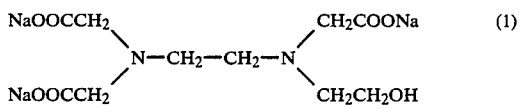

This previous procedure generated $Na_2SO_4$ as a by-product which was removed by filtration, after a costly brine cooling, as the decahydrate salt. Yield losses during the $Na_2SO_4.10H_2O$ filtration were approximately 10°-20%. Also the product solution was found to precipitate additional $Na_2SO_4$ during subsequent storage and/or shipment. The $Na_2SO_4$ removed was disposed in land fill as there is little economic demand for such impure "salt-cake".

Ferric HO-EDTA can also be prepared from ferric nitrate. The product is more expensive than that prepared from $Fe_2(SO_4)_3$ but is more stable concerning sedimentation of sodium sulfate.

THE INVENTION

The procedure of this invention is based on the oxidation of elemental Fe by nitric acid in the presence of HO-EDTA.Na₃ to generate a ferrous chelate with iron in the +2 oxidation state. This chelate is then oxidized to the ferric chelate ($Fe^{+3}$) by a gaseous oxygen source.

The equations governing these oxidations are as follows:

Fe Oxidation: (I)

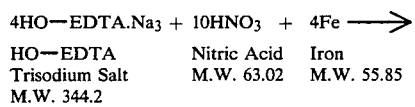

| HO—EDTA | Nitric Acid | Iron |
| Trisodium Salt | M.W. 63.02 | M.W. 55.85 |
| M.W. 344.2 | | |

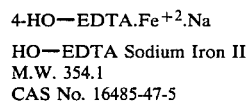

4-HO—EDTA.Fe$^{+2}$.Na
HO—EDTA Sodium Iron II
M.W. 354.1
CAS No. 16485-47-5

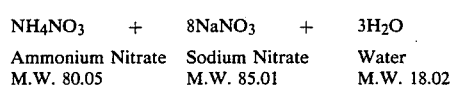

| Ammonium Nitrate | Sodium Nitrate | Water |
| M.W. 80.05 | M.W. 85.01 | M.W. 18.02 |

Ferrous Oxidation: (II)

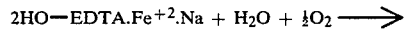

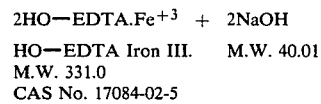

HO—EDTA Iron III.   M.W. 40.01
M.W. 331.0
CAS No. 17084-02-5

The iron oxidation (Equation I) is performed by adding Fe° in powder form incrementally to a mixture of the nitric acid and an aqueous solution (40-50 wt. %) HO-EDTA.Na₃. About two thirds of the HO-EDTA.Na₃ required for stoichiometric combination with the iron is used. The alkalinity of the sodium salt raises the pH sufficiently to enable control of this oxidation reaction provided that the temperature is kept below about 75° C. The rate of iron addition combined with air or water cooling can provide such temperature control.

After completion of the iron oxidation (Equation I) the rest of the HO-EDTA.Na3 required to chelate the oxidized iron is added. This $Fe^{+2}$ chelate solution is then heated to about 90° C. and the ferrous to ferric oxidation (Equation II) is initiated and continued to completion by intimate contact with a gaseous $O_2$ source. The preferred and cheapest of such sources is air, sparged through the mixture, but pure oxygen or any other source of gaseous oxygen capable of sparging through the mixture will suffice.

Upon completion of this last oxidaton, the pH, balance and assay of the product are adjusted and the solution filtered of iron oxide impurities.

DETAILED DESCRIPTION

The commercially available HO-EDTA.Na3 has a pH of about 10. It is a 40-50% aqueous solution. The nitric acid is added to this salt slowly with stirring to prevent localized heating. The exotherm during this addition raises the temperature of the resulting mixture about 45° C. The pH of the mixture is adjusted to about 1.2. About two thirds of the stoichiometric amount of HO-EDTA.Na3, based on iron, is thus mixed with $HNO_3$.

The $HNO_3$/HO-EDTA.Na3 mixture is then cooled to about 50° C. and the addition of Fe is initiated. The preferred form is a less than 60 mesh iron powder.

The iron powder is slowly added to the stirred nitrated mixture at a rate that the exotherm will not heat the mixture to above about 70° C., but preferably the mixture should be about 50°-60° C. The Fe oxidation and solution reaction is exothermic but under the mild condition mentioned (50°-60° C.; pH 1-2) the reduction product is primarily $NH_4NO_3$. At higher temperatures (above about 70°-75° C.) it can include $H_2$ and $NO_x$. The exotherm can also be more vigorous if the pH is below 1 or the temperature above 75° C. at which points some oxidation of the organic materials may start.

The iron is preferably added at 10 minute intervals, providing sufficient time for the exotherm to be dissipated by air cooling or if necessary by water-jacket cooling. Two hours are sufficient for the complete addition of iron. Upon completion of the addition, the mixture pH is about 1.8.

At this point in the process, there is approximately two thirds of the HO-EDTA in solution required for chelation of the iron as $Fe^{+3}$. The air oxidation of unchelated $Fe^{+2}$ to $Fe^{+3}$ is thermodynamically unfavorable in aqueous solution.

Since the $Fe^{+3}$ is more strongly chelated than $Fe^{+2}$, the presence of HO-EDTA will shift the reaction equilibrium in favor of the $Fe^{+3}$ oxidation state. Consequently, more HO-EDTA is added before beginning air-oxidation. When the addition of the rest of the required HO-EDTA is completed, the mixture is heated to 90° C. and the air oxidation is started.

The total HO-EDTA charge is about 95 to 100% of the stoichiometric requirement for combination with the dissolved iron. Air or another oxygen source is then bubbled through the solution with stirring.

During air sparging the solution gradually changes from dark green to dark red. The progress of the oxidation is conveniently followed by titrating samples with $0.1N$ $Ce(SO_4)_2$ using Ferrion indicator (modified Hunt method). A 1 ml aliquot is added to 75 Ml 7N $H_2SO_4$ and then titrated. When the $Fe^{+2}$ concentration drops below 0.1 wt. %, the color of the solution of the aliquot is $H_2SO_4$ is nearly colorless, versus a pale green color for higher $Fe^{+2}$ concentrations. This simple color test provides a convenient guide for following the ferrous→ferric air oxidation (Equation II). As mentioned above, while air is preferred as the oxidant, any other gaseous oxygen source including pure oxygen or means for generating nascent oxygen may be used.

The time needed for completion of the $Fe^{+2}$ oxidation to the $Fe^{+3}$ chelate is dependent on the rate of agitation and the rate of oxygen availability as the process is clearly mass-transfer controlled. The final pH upon completion is in the range 5.2 to 5.8.

The balance of the product, to meet commercial specifications, is then completed (0.1-1.0 wt. % excess HO-EDTA). Slight adjustments of the pH can be made to meet specification by the addition of either $HNO_3$ or HO-EDTA.Na3.

The assay of the product is adjusted to 5.0-5.5 wt. % Fe by adding water as needed. The final solution is polish filtered to remove any unreacted iron, probably iron oxide from the starting material.

The process of this invention is about one-third cheaper in material charges than the previous process using 50% $Fe_2(SO_4)_3$ and HO-EDTA.Na3. Direct time and labor charges are much lower and of course the brine cooling for crystallization of impurities is completely eliminated.

From the environmental point of view approximately 8 lbs of residue, primarily iron oxides, per 1000 lbs are filtered from the final product for disposal. The preferred disposal is by burial. This residue is benign by the usual tests.

Approximately 9 pounds of $NO_x$ vapors per 1000 pounds are generated during the air oxidation step. These vapors are predominantly $NO_2$, since NO is readily converted to $NO_2$ in the presence of excess oxygen. Most of the $NO_2$ is observed in the last 30 minutes of the air oxidation step when the bulk of the $Fe^{+2}$ has already been coverted to $Fe^{+3}$ (total $Fe^{+2}$ less than 1 wt. %). This may indicate the start of oxidation of the organics. The $NO_2$ is effectively absorbed in an aqueous scrubber where it is converted to dilute nitric acid.

Tests for evidence of corrosion of reaction vessel materials during the two extremes of the reaction process i.e. during the initial nitration when the pH was lowest; and during the air oxidation at 90° C. indicate that the entire process can be run in 316 SS vessels.

The process in its various preferred aspects, depending on batch size, is described in the appended examples. All art-recognized, equivalent, alternate materials and process steps are intended.

EXAMPLE 1

By a dropping funnel 252 g of 70% $HNO_3$ was added to 470 gm of HO-EDTA.Na3 solution (44.8% trisodium salt) (CHEL DM$^R$) in a glass reactor. The exotherm increased the temperature about 45° C. during the addition. The pH dropped from about 10 to about 1.2.

When the batch, cooled to about 50° C., 54.7 gm of Fe(-40 mesh) was added incrementally over a two hour period. A slight exotherm occurred after each addition. Adding the Fe at 10 minute intervals was sufficient to permit dissipation of the exotherm by air cooling of the reactor. After completion of the iron addition, all of the iron was dissolved to form a deep green aqueous solution of the $Fe^{+2}$ chelate.

An additional 174 gm of HO-EDTA.Na3 was added to the batch (completing 95% of the stoichiometric requirements, based on iron) and the batch was heated to 90° C. Air was then bubbled through the solution with stirring.

During the air sparging, the solution color gradually changed from dark green to dark red. The progress of the oxidation was followed by the Hunt method. At least 2.5 hrs. was required to oxidize all the $Fe^{+2}$. At this stage the batch was balanced to 0.1–1.0 wt. % excess HO-EDTA. The pH was adjusted to 5.2–5.8 with $HNO_3$ or the sodium salt. After filtration the assay was adjusted to 5.0 to 5.5 wt % Fe by adding water.

Yield 96% based on HO-EDTA.

EXAMPLE 2

In a 2000 gal. SS reactor, 850 gal. of 43 wt % HO-EDTA.Na₃ solution (CHEL®DM) was charged. Cooling water was circulated in the jacket of the reactor, and the reaction mass was stirred. Then 450 gal. of 67 wt % $HNO_3$ was added. The pH wa 1.0–1.4 after addition of the nitric acid.

The batch was cooled to 50°–55° C. Powdered Fe(−60 mesh) was charged in 100 lb increments every 10 minutes. A total of 1150 lb of Fe (90% assay) was charged. The temperature gradually increased to 75°–80° C. during the Fe addition with full cooling water on the jacket. To insure complete reaction of the Fe, the reaction mass was agitated for a further 20–30 minutes without cooling water after completion of the Fe addition.

An additional 340 gal. of CHEL®DM solution was added raising the pH to 3.5–4.5. The solution was then concentrated somewhat by applying steam to the jacket and boiling off approximately 150 gal. of $H_2O$. It was generally necessary to concentrate plant batches relative to lab batches because of a lower rate of water loss during the air-sparge step for the plant. It is important to concentrate before the air sparge step rather than after because of the decomposition of HO-EDTA in the presence of $Fe^{+3}$ when refluxing. No decomposition occurs, however, when the reflux is performed with iron in the +2 oxidation state.

After concentration, the batch was cooled to about 90° C. and air sparging initiated. Approximately 7 hours was required to air sparge to an $Fe^{+2}$ concentration of less than 0.1 wt %. There was no cooling water on the jacket during the air sparge, and the batch temperature gradually dropped to 60°–70° C.

At the conclusion of the air sparge, the balance was adjusted to 0.1–1.0 wt % excess HO-EDTA. The pH was adjusted to 5.2–5.8 with $HNO_3$, CHEL®DM or caustic as needed. After clarification through a Durco filter, the assay was adjusted to 5.0–5.5 wt % Fe with water.

Yield 98.0±4.3% based on HO-EDTA.

What is claimed is:

1. A process for preparing ferric HO-EDTA which comprises the steps of
    (a) adding nitric acid to an aqueous solution of about two thirds of the stoichiometric equivalent of trisodium N-(2-hydroxyethyl)ethylenediaminetriacetic acid based on Fe, reacting therewith to form a solution of pH about 1.0 to 1.4;
    (b) adding powdered iron to said solution while maintaining the resulting reaction mixture at below about 70° C. to form a ferrous chelate;
    (c) adding an amount of said trisodium N-(2-hydroxyethyl)ethylenediaminetriacetic acid sufficient to complete the stoichiometric requirement therefor;
    (d) contacting the resulting ferrous chelate mixture, maintained at temperatures in the range 50°–90° C., with an oxygen source to initiate and complete oxidation of the ferrous chelate to ferric chelate;
    (e) adjusting the resulting ferric chelate solution to about pH 5.0–6.0 containing less than about 1% free HO-EDTA, and 5.0 to 5.5 wt. % Fe in ferric chelated form.

2. The process according to claim 1 wherein said $HNO_3$/HO-EDTA.Na₃ solution has a pH of substantially 1.2.

3. The process according to claim 1 wherein said iron powder is less than 40 mesh.

4. The process according to claim 1 wherein said ferrous chelate is a green aqueous solution.

5. The process according to claim 1 wherein said solution is concentrated in the absence of $Fe^{+3}$.

6. The process according to claim 1 wherein said contacted oxygen source is sparged air.

7. The process according to claim 1 wherein the oxygen source is pure oxygen.

8. The process according to claim 1 where said ferric chelate solution is a red aqueous solution containing 29–33 wt. % of ferric HO-EDTA.

* * * * *